United States Patent [19]

Rittner et al.

[11] Patent Number: 4,918,225
[45] Date of Patent: Apr. 17, 1990

[54] PROCESS FOR THE PREPARATION OF PURE CROTONIC ACIDS

[75] Inventors: Siegbert Rittner, Mörfelden-Walldorf; Herbert Görtz, Frankfurt am Main; Knut Riedel, Hofheim am Taunus, all of Fed. Rep. of Germany

[73] Assignee: Hoechst Aktiengesellschaft, Frankfurt am Main, Fed. Rep. of Germany

[21] Appl. No.: 783,319

[22] Filed: Oct. 2, 1985

Related U.S. Application Data

[63] Continuation of Ser. No. 558,112, Dec. 5, 1983, abandoned.

[30] Foreign Application Priority Data

Dec. 7, 1982 [DE] Fed. Rep. of Germany ....... 3245111

[51] Int. Cl.$^4$ ...................... C07C 51/43; C07C 57/08
[52] U.S. Cl. ..................... 562/600; 562/598
[58] Field of Search ................. 562/600, 598

[56] References Cited

U.S. PATENT DOCUMENTS 3,375,082 3/1968 Graf et al. .................. 23/295 R

FOREIGN PATENT DOCUMENTS 881566 9/1971 Canada ............................... 562/598

OTHER PUBLICATIONS

Kirk–Othmer, Encyclopedia of Chemical Technology, 2nd ed., vol. 6, John Wiley & Sons Inc., N.Y., 1965, pp. 464–467.

*Primary Examiner*—Vivian Garner
*Attorney, Agent, or Firm*—Curtis, Morris & Safford

[57] ABSTRACT

The invention relates to a process for the preparation of pure cis- or trans-crotonic acid from a mixture of the two isomers by melt crystallization. To prepare trans-crotonic acid, an isomer mixture I containing at least 40% by weight of trans-crotonic acid is used as the starting material. On the other hand, if cis-crotonic acid is to be prepared, an isomer mixture II containing at least 80% by weight of cis-crotonic acid is used as the starting material. The particular isomer mixture is melted and then left to cool, trans-crotonic acid being allowed to crystallize out of mixture I to a residual content of at least 35% by weight, and cis-crotonic acid being allowed to crystallize out of mixture II to a residual content of at least 75% by weight.

2 Claims, No Drawings

PROCESS FOR THE PREPARATION OF PURE CROTONIC ACIDS

This application is a continuation of application Ser. No. 558,112, filed Dec. 5, 1983, now abandoned.

The reaction mixture obtained an oxidation of crotonaldehyde with air or oxygen contains over 90% by weight of trans-crotonic acid, after the unreacted crotonaldehyde has been distilled off. The remainder is chiefly cis-crotonic acid, together with small amounts of crotonaldehyde, formic acid, acetic acid and propionic acid.

In order to obtain pure trans-crotonic acid, for example for use as a monomer for polymers or as a builder unit for syntheses, from this mixture, the mixture is worked up, according to the prior art, in a two-stage purification operation comprising fractional distillation and crystallization from water (Winnacker-Küchler, Chemische Technologie, 3rd edition, volume 4, 1972, page 107; Ullmanns Enzyklopädie der technischen Chemie (Ullmann's Encyclopedia of Industrial Chemistry), 4th edition, volume 9, 1975, page 145).

However, during the crystallization from water, about one ton of highly contaminated effluent which must be purified biologically is formed per ton of transcrotonic acid. This is also accompanied by about 1,500 m$^3$ (S.T.P.) of air, from the drying of the water-moist trans-crotonic acid, per ton of trans-crotonic acid, and this air must also be purified. Furthermore, the crystallization from water also causes product losses and, finally, drying of the water-moist crotonic acid requires considerable amounts of energy.

Surprisingly, it has now been found that these disadvantages are avoided if crystallization is effected from the melt instead of from water. In this manner, not only can trans-crotonic acid be isolated, but cis-crotonic acid can also be isolated under mild conditions and in a high purity.

The present invention relates to a process for the preparation of pure trans-crotonic acid from a mixture of the two isomeric crotonic acids containing at least 40% by weight of trans-crotonic acid, which comprises melting the mixture and then leaving trans-crotonic acid to crystallize out, by cooling, as long as the proportion thereof in the melt is still at least 35% by weight.

The present invention also relates to a process for the preparation of pure cis-crotonic acid from a mixture of the two isomeric crotonic acids containing at least 80% by weight of cis-crotonic acid, which comprises melting the mixture and then leaving cis-crotonic acid to crystallize out, by cooling, as long as the proportion thereof in the melt is still at least 75% by weight.

The great advantage of the process according to the invention is that no effluent or waste air problems arise. Moreover, energy is saved, since drying of the water-moist crotonic acid is eliminated and just water is sufficient as the cooling medium.

The cis/trans isomer mixture containing at least 40% by weight of trans-crotonic acid which is required for the preparation of pure trans-crotonic acid can be obtained, for example, from the reaction product of the crotonaldehyde oxidation by simply distilling off the unreacted crotonaldehyde. On the other hand, if the cis-crotonic acid is to be isolated from the above reaction product, its contents therein being only 3 to 4% by weight, a cis/trans isomer mixture containing at least 80% by weight of cis-crotonic acid must first be isolated from the reaction product by fractional distillation, and can then be used according to the invention.

The particular crotonic acid can be crystallized out of the melt either discontinuously, for example in a tube crystallizer (so-called drip apparatus), or semicontinuously or continuously. If particular purity is required, the melt crystallization according to the invention can be repeated once or several times.

The pure to highly pure crotonic acids obtained are useful products; apart from being suitable as monomers for polymer compounds, they can be used, for example, as builder units for the synthesis of pharmaceuticals, dyes, pesticides or textile assistants.

The process according to the invention is illustrated by the following examples.

EXAMPLE 1

A crotonic acid mixture (from the distillation of the reaction product of the oxidation of crotonaldehyde) with a solidification point of 59° C. and the composition shown below is used in a tube crystallizer, the jacket of which is connected to a thermostat:

| | |
|---|---|
| trans-crotonic acid: | 94.5–95.5% |
| cis-crotonic acid: | 3–4% |
| crotonaldehyde: | 0.6% |
| formic acid, acetic acid, propionic acid: | 0.7% |

The melt is cooled to 56°–57° C. and is left to crystallize at this temperature for four hours. It is then cooled to 10° C. in the course of 8 hours. The liquid remaining in the apparatus is subsequently drained off, and the temperature of the contents remaining in the apparatus is slowly increased, until the solidification point of the melt draining off is 70.8° C.

The light crystals which remain in the apparatus are melted and the melt is isolated. About 116 parts by weight of the above starting mixture from the distillation of crotonic acid are required per 100 parts by weight of pure trans-crotonic acid. The pure trans-crotonic acid isolated has the following characteristic values:

| | |
|---|---|
| solidification point: | 71.4° C. |
| % of trans-crotonic acid: | 99.9 |
| % of cis-crotonic acid: | 0.1 |
| color number (Hazen): | 0–5 |

EXAMPLE 2

A cis/trans crotonic acid mixture which contains 90% of cis-crotonic acid, has a solidification point of +8.1° C. and has been prepurified by fractional distillation is introduced into the same tube crystallizer as described in Example 1. The melt is cooled to 6°–7° C. and is seeded with a few cis-crotonic acid crystals at this temperature. When the melt has crystallized completely, the temperature is kept at 5° C. for two hours and the mixture is then reduced slowly to −3° C. The liquid remaining in the apparatus is then drained off and the crystals are purified by slowly increasing the temperature up to about +13.5° C.

The light crystals which remain in the apparatus are melted and the melt is isolated. About 164 parts by weight of the feed material of the above composition are required per 100 parts by weight of pure cis-crotonic acid. The pure cis-crotonic acid obtained has the following characteristic values:

| solidification point: | 14.6° C. |
|---|---|
| purity, determined by NMR: | 99.8% |

We claim:

1. A process for the preparation of pure trans-crotonic acid from a mixture of trans-crotonic acid and cis-crotonic acid containing at least 40% by weight of trans-crotonic acid, which comprises melting the mixture and crystallizing trans-crotonic acid from the melted mixture by cooling the melted mixture as long as the melted mixture contains at least 35% by weight of trans-crotonic acid.

2. A process for the preparation of pure cis-crotonic acid from a mixture of trans-crotonic acid and cis-crotonic acid containing at least 80% by weight of cis-crotonic acid, which comprises melting the mixture and crystallizing cis-crotonic acid from the melted mixture by cooling the melted mixture as long as the melted mixture contains at least 75% by weight of cis-crotonic acid.

* * * * *

UNITED STATES PATENT AND TRADEMARK OFFICE
CERTIFICATE OF CORRECTION

PATENT NO. : 4,918,225
DATED : April 17, 1990
INVENTOR(S) : Siegbert Rittner, et al.

It is certified that error appears in the above-identified patent and that said Letters Patent is hereby corrected as shown below:

Column 1, line 7, "an" should be --on--.

Signed and Sealed this

Fourth Day of February, 1992

Attest:

HARRY F. MANBECK, JR.

*Attesting Officer*  *Commissioner of Patents and Trademarks*